United States Patent
Fukuda et al.

(10) Patent No.: US 7,217,365 B2
(45) Date of Patent: May 15, 2007

(54) BLOOD FILTRATION METHODS (75) Inventors: Tatsuya Fukuda, Oita (JP); Morikazu Miura, Oita (JP)

(73) Assignee: Asahi Kasei Medical Co., Ltd., Tokyo (JP)

( * ) Notice: Subject to any disclaimer, the term of this patent is extended or adjusted under 35 U.S.C. 154(b) by 139 days.

(21) Appl. No.: 10/475,987

(22) PCT Filed: Apr. 26, 2002

(86) PCT No.: PCT/JP02/04201

§ 371 (c)(1),
(2), (4) Date: Apr. 14, 2004

(87) PCT Pub. No.: WO02/087660

PCT Pub. Date: Nov. 7, 2002

(65) Prior Publication Data

US 2004/0200775 A1 Oct. 14, 2004

(30) Foreign Application Priority Data

| Apr. 26, 2001 | (JP) | ............................ 2001-129176 |
| Apr. 26, 2001 | (JP) | ............................ 2001-129177 |
| Aug. 31, 2001 | (JP) | ............................ 2001-262539 |

(51) Int. Cl.
*B01D 37/00* (2006.01)

(52) U.S. Cl. .................. 210/649; 210/767; 210/800; 210/806

(58) Field of Classification Search ................ 210/252, 210/257.1, 258, 435, 767, 782, 787, 789, 210/739, 740, 745, 649, 800, 806; 494/37
See application file for complete search history.

(56) References Cited

U.S. PATENT DOCUMENTS

| 4,985,153 A | * | 1/1991 | Kuroda et al. | ............... 210/782 |
| 5,100,564 A | * | 3/1992 | Pall et al. | ................... 210/782 |
| 5,594,164 A | * | 1/1997 | Bull | .......................... 73/61.66 |
| 5,690,815 A | * | 11/1997 | Krasnoff et al. | ............... 210/97 |

FOREIGN PATENT DOCUMENTS

| JP | 05-322886 | 12/1993 |
| JP | 2000-334034 | 12/2000 |
| WO | WO 92/07656 | * 5/1992 |

* cited by examiner

*Primary Examiner*—John Kim
(74) *Attorney, Agent, or Firm*—Young & Thompson (57) ABSTRACT

Methods wherein a blood cell concentration gradient is formed in a pooling unit in which blood is pooled before or after introducing the blood into a filter for eliminating leukocytes followed by the filtration are disclosed. By the first method comprising forming a blood cell concentration gradient in the pooling unit before introducing blood into the filter for eliminating leukocytes followed by the filtration, leukocytes can be efficiently eliminated from a whole blood preparation or a high platelet collection ratio can be established while maintaining a high leukocyte elimination ratio. By the second method comprising forming a blood cell concentration gradient in the pooling unit after introducing blood into the filter for eliminating leukocytes followed by the filtration, leukocytes can be efficiently eliminated from a whole blood preparation or a platelet preparation and platelets can be collected at a high ratio.

11 Claims, 4 Drawing Sheets

BLOOD FILTRATION METHODS

TECHNICAL FIELD

The present invention relates to a blood filtration method and a blood filtration apparatus for removing leukocytes from blood using a leukocyte-removing filter.

BACKGROUND ART

Because of recent progress in the blood transfusion medical science, blood component transfusion that transfuses only components necessary for a recipient is mainly employed in the present blood transfusion medical treatment. Advantages such as a relieved burden on a recipient and an increased curing effect are given as the reasons for wide acceptance of the blood component transfusion. Blood component products, which are used for the transfusion, such as a concentrated erythrocyte product, concentrated platelet product, and blood plasma product, are prepared by centrifuging a whole blood product obtained by blood donation. A large amount of leukocytes is contained in blood products prepared in this manner. It has been discovered that such contained leukocytes induce comparatively slight side effects, such as headache, nausea, chills, and an non-hemolytic febrile transfusion reaction, as well as serious side effects, such as alloantigen sensitization, virus infection, and post-blood transfusion GVHD that seriously affect a recipient. For this reason, leukocyte-removing filters packed with a filter material such as a fiber material or porous material containing continuous pores has been widely used.

Removal of leukocytes using a leukocyte-removing filter includes the case where the leukocytes are removed from a whole blood product and the case where the leukocytes are removed from each blood component product that has been prepared. In the latter case, a filter is required for each blood component product. On the other hand, the former case is regarded to be more preferable, since leukocytes are removed from a whole blood product and the whole blood product from which the leukocytes have been removed is centrifuged to produce different and several kinds of blood component products not containing leukocytes.

Particularly, in recent years, a closed system prepared by integrating a bag for whole blood products, filters, bags for various blood component products that are obtained after centrifugal separation, and the like, to produce blood component products from which leukocytes have been aseptically removed has attracted attention and is used at blood centers and the like (Japanese Patent Application Laid-open No. 320064/1989, etc.).

In the method for preparing blood free from leukocytes using a filter such as a closed system commonly employed in blood centers and the like, a system in which bags for blood containing a large amount of leukocytes, a filter, and bags for collecting filtered blood, and the like are connected with each other via soft tubes made from vinyl chloride or the like may be used. More specifically, bags containing blood still containing un-removed leukocytes are hung on a rack with hooks and the like for a head drop of about 0.5–2 m, where the blood containing un-removed leukocytes is thoroughly mixed to homogenize. Thereafter, a clamp or a breakable seal in the tube is manually released to collect blood from which leukocytes have been removed in the recovery bag through a filter. The operation is substantially continuously conducted to minimize a burden on filtration operators.

A currently commercially available closed system for filtering a whole blood product removes leukocytes and plasma. Therefore, two blood component products from which leukocytes have been removed, a concentrated erythrocyte product and a plasma product, can be eventually obtained.

Since a whole blood product contains a large amount of leukocytes, a large capacity is required for the filter to remove leukocytes to the same degree as that achieved when removing leukocytes from each blood component product. However, an increase in the filter capacity results in an increase in the amount of blood that remains in the filter. Since the remaining blood is discarded together with the filter after filtration, an increased filter capacity has a problem of an increase in the loss of precious blood.

In addition, usually only a fresh whole blood product within three days at most and in many cases within several hours after collection is filtered for separation. Leukocytes removing capability of a filter is known to decrease when filtering a whole blood product that is very fresh and has a high temperature, in particular, within one hour after collection.

In view of these problems remaining still to be solved for efficiently removing leukocytes from a whole blood product, establishment of a blood filtering method that can remove leukocytes efficiently and at a high rate has been strongly desired.

In addition, a functional filter that can selectively remove only leukocytes from a whole blood product and recover platelets together with erythrocyte and plasma is being developed in recent years (Transfusion vol. 39 (1999), No. 10S, Supplement, S541-040K, S542-040K).

Three blood component products from which leukocytes have been removed, a concentrated leukocyte-free erythrocyte product, concentrated platelet product, and plasma product, can be eventually obtained by filtrating a whole blood product using such a filter. However, since platelets included in a fresh whole blood product are slightly activated due to a stress or the like during blood collection and are caused to easily to adhere to a filter, the technology cannot attain the level to ensure a high platelet recovery rate in a stable manner at the present time.

Japanese Patent No. 2521090 discloses a filter in which the filter material is maintained under wet conditions of saturated water content or more with an aqueous solution of a water-soluble substance harmless to water or living bodies. This technology reduces adhesion of platelets by wetting the filter material with an aqueous solution such as a physiological saline solution and increases the platelet recovery rate. However, according to investigations by the inventors of the present invention, a satisfactory increase in the platelet recovery rate was not achieved while maintaining high leukocyte removal capability. In addition, since the above disclosed filter is previously wetted with a physiological saline solution or the like, air that may be accidentally introduced in the filter not only can be discharged to outside the apparatus only with difficulty, but also may decrease or suspend the blood flow.

A method of fractionating a whole blood product into blood component products by centrifugation and filtering each blood component product is also known. For example, Japanese Patent Application Laid-open No. 2000-334034 discloses a method of subjecting a whole blood product to a very strong centrifugation of 3,520×g to separate the blood into three components, plasma, a buffy coat with a large platelet content, and concentrated erythrocytes, and sequentially filtering the buffy coat and concentrated erythrocytes using one filter. Two component blood products from which leukocytes have been removed, one a concentrated platelet product and the other a concentrated erythrocyte product, and a plasma product from which leukocytes have not been removed can be ultimately prepared using this method. However, according to investigations of the present inventors, such strong centrifugation activates platelets making it difficult to recover platelets at a satisfactory yield. In addition, the plasma product has a problem not to be removed leukocytes.

WO 92/07656 discloses a method and system of separating a whole blood obtained by blood collection into a concentrated erythrocyte product and platelet-rich plasma by weak centrifugation and filtering these separated fractions through different filters. Although leukocytes can be removed from all ultimately obtained blood component products according to the method, this method requires a complicated procedure of inserting two filters together with a plurality of bags into a centrifuge cup. In addition, use of two filters increases the cost.

A filter for selectively removing leukocytes from a whole blood product or a platelet product, such as platelet-rich plasma product or a concentrated platelet product prepared by a blood component collection apparatus, is commercially available and used in blood centers or clinical work front. Although some portion of platelets having high adhesion can be recovered by using this filter, the platelet recovery rate varies depending on individual difference of bloods and the like. Therefore, stability of the platelet recovery rate is still to be improved.

In this manner, there are many subjects to be improved in the existing technology for removing leukocytes from a whole blood product or the technology for recovering platelets from a whole blood product or a platelet product originating from a whole blood product or blood component collection while removing leukocytes. Development of a blood filtration method having an improved leukocytes removing capability so that a need for increasing filter capacity may not be required, exhibiting an increased recovery rate of platelets if the platelets are recovered, and being easily operated has been desired.

Since leukocytes removal has been recognized to be effective for safe transfusion, the amount of blood processed for removing leukocytes in blood centers and the like is increasing year by year. Automatic blood filtration has been desired to relieve burden loaded on operators processing a large amount of blood. Development to satisfy this requirement is ongoing.

Japanese Patent Application Laid-open No. 10-212237 discloses an apparatus for automatic filtration in which blood is filtered at a constant flow rate by using a pump. The apparatus maintains an appropriate flow rate of the filtered blood while monitoring pressure near the filter inlet port and controlling operation of the pump according to the pressure.

Japanese Patent Application Laid-open No. 09-108334 discloses an apparatus that can detect the fact that a predetermined amount of blood has been processed using a timer, a sensor to optically detect the blood surface or the gas/blood interface, a weight sensor to detect the amount of blood, a pressure sensor to detect the pressure of a tube, and the like, to automatically suspend filtration.

An automatic filtration apparatus in which not only is the blood filtration process automated, but also the blood filtration data (filtration time, temperature, flow rate, etc.) can be recoded by a computer has been developed to satisfy the requirements for quality control of blood products that has become more stringent than ever (Vox Sanguinis Vol. 78 (Supplement 1), 2000, P517, P518). An excellent feature of the apparatus is its capability of simultaneously automatically filtering 40 bloods while automatically homogenizing the bloods before or even during filtration by a mechanical means, and the capability of automatically recording filtration data, and the like.

The above automatic apparatuses have been developed with an objective of automatically filtering blood in a homogeneous state, automatically filtering at a constant flow rate of blood, and automatically suspending filtration operation. The blood filtration apparatus of the present invention is an automatic filtration initiate equipment suitable for implementing a blood filtration method for improving performance of the filter of the present invention and differs from the above-described automatic filtration apparatuses.

The features of the blood filtration method and automatic filtration apparatus of present invention will be described in more detail.

DISCLOSURE OF THE INVENTION

A first object of the present invention is to provide a blood filtration method that can exhibit improved filtration performance and is easy to be operated. More specifically, the present invention provides a blood filtration method that can efficiently remove leukocytes from a very fresh whole blood product without increasing the filter capacity or can stably achieve a high platelet recovery rate while maintaining a high leukocyte removing capability when processing a whole blood product or a platelet product derived from a whole blood product or a blood component collection. As a result of extensive studies, the inventors of the present invention have found that the above first object can be achieved by a method of filtering a blood that has been brought into an inhomogeneous state in which a blood cell concentration gradient has been formed in a storing unit for storing the blood represented by a blood bag.

A second object of the present invention is to provide an automatic filtration initiate apparatus suitable for use in the blood filtration method of the present invention. The inventors of the present invention have found that the above second object can be achieved by a blood filtration apparatus provided with a signal transmitting means that can emit signals after an appropriate blood cell concentration gradient has been formed and an operation means that can automatically release a flow control means based on the signals from the signal transmitting means.

The objects of the present invention can be achieved by the following blood filtration methods and blood filtration apparatuses:

(1) a blood filtration method for removing leukocytes from blood comprising forming a blood cell concentration gradient in a storing unit for storing the blood, filtering the blood through a leukocyte-removing filter, and collecting the filtered blood in a recovery unit, (2) the blood filtration method described in (1) above, wherein the blood cell concentration gradient is previously formed in the storing unit before filling the filter with blood, (3) the blood filtration method described in (1) or (2) above, wherein the blood cell concentration gradient is formed by allowing the blood to stand for a predetermined period of time, (4) the blood filtration method described in (3) above, wherein the blood cell concentration gradient is formed by allowing the blood to stand for not less than 5 minutes to less than 300 minutes, (5) the blood filtration method described in (1) or (2) above, wherein the blood cell concentration gradient is formed by weak centrifugation, (6) the blood filtration method described in (5) above, wherein the blood cell concentration gradient is formed by weak centrifugation at a centrifugal force of not less than $100 \times g$ to not more than $1,200 \times g$ for not less than 0.3 minutes to not more than 10 minutes, (7) the blood filtration method described in (5) or (6) above, wherein the blood cell concentration gradient is formed by weak centrifugation, and then the blood is allowed to stand for a predetermined period of time, (8) the blood filtration method described in (1) above, wherein the blood cell concentration gradient is formed in the storing unit after filling the filter with blood, (9) the blood filtration method described in (1) or (8) above, wherein the blood cell concentration gradient is formed by controlling the blood flow rate for a predetermined period of time, (10) the blood filtration method described in (9) above, wherein the blood cell concentration gradient is formed by controlling the blood flow rate not less than 5 minutes to less than 300 minutes, (11) the blood filtration method described in any one of (1) to (10) above, wherein the blood is a fresh whole blood product, (12) the blood filtration method described in any one of (1) to (11) above, wherein the blood is introduced into the leukocyte-removing filter from a lower part of the storing unit after forming an erythrocyte concentration gradient so that the hematocrit value of the blood in the lower part of the storing unit is larger than the hematocrit value of the whole blood product in the storing unit that has been uniformly homogenized, (13) the blood filtration method described in (12) above, wherein the hematocrit value of the blood in the lower part of the storing unit is not less than 1.05 times to less than 2.50 times the hematocrit value of the whole blood product in the storing unit that has been uniformly homogenized, (14) the blood filtration method described in (12) or (13) above, wherein the hematocrit value of the blood in the lower part of the storing unit is not less than 35% to less than 75%, (15) the blood filtration method described in any one of (11) to (14) above, wherein the blood cell separation degree of the blood in the storing unit after forming the blood cell concentration gradient is not less than 3% to less than 60%, (16) the blood filtration method described in (8) above, wherein the blood is a platelet product, (17) the blood filtration method described in any one of (1) to (16) above, wherein leukocytes are selectively removed and platelets are allowed to pass through, (18) the blood filtration method described in any one of (1) to (17) above, wherein the blood is filtered through one leukocyte-removing filter, (19) in a blood filtration apparatus comprising at least a storing unit for storing blood, a holding unit for holding the storing unit, a leukocyte-removing filter, a recovery unit for collecting blood filtered through the leukocyte-removing filter, a first connecting tube connecting the storing unit with the leukocyte-removing filter, and a second connecting tube connecting the leukocyte-removing filter with the recovery unit, the blood filtration apparatus characterized by further comprising a flow control means for controlling a blood flow installed in the first connecting tube and/or the second connecting tube, a signal transmitting means worked in conjunction with the flow control means, and an operation means that can automatically release the flow control means based on the signals from the signal transmitting means, (20) the blood filtration apparatus described in (19) above, wherein signals are emitted from the signal transmitting means after the storing unit has been held by the holding unit and allowed to stand for a predetermined period of time, (21) the blood filtration apparatus described in (20) above, wherein signals are emitted from the signal transmitting means after the storing unit has been held by the holding unit and allowed to stand for not less than 5 minutes to less than 300 minutes, (22) the blood filtration apparatus described in (19) above, wherein signals are emitted from the signal transmitting means after the storing unit containing blood after weak centrifugation has been held by the holding unit and allowed to stand for a predetermined period of time, (23) the blood filtration apparatus described in (22) above, wherein signals are emitted from the signal transmitting means after the storing unit containing blood after weak centrifugation at a centrifugal force of not less than $100 \times g$ to not more than $1,200 \times g$ for not less than 0.3 minutes to not more than 10 minutes has been held by the holding unit and allowed to stand for a predetermined period of time, (24) the blood filtration apparatus described in (19) above, wherein signals are emitted from the signal transmitting means after the blood has been filled in the filter and the flow rate has been allowed to be controlled for a predetermined period of time, (25) the blood filtration apparatus described in (24) above, wherein signals are emitted from the signal transmitting means after the blood has been filled in the filter and the flow rate has been allowed to be controlled for not less than 5 minutes to less than 300 minutes, (26) the blood filtration apparatus described in any one of (19) to (25) above, wherein signals are emitted from the signal transmitting means after the blood separation degree has reached not less than 3% to less than 60%, (27) the blood filtration apparatus described in any one of (19) to (25) above, wherein the signal transmitting means is a timer, and (28) The blood filtration apparatus described in any one of (19) to (26) above, wherein the signal transmitting means is an optical sensor.

The blood filtration method of the present invention will be described in detail.

Blood cells contained in blood have a specific gravity varying according to the type of blood cells. Erythrocytes are known to have a specific gravity of about 1.08; granulocytes and monocytes, about 1.07; lymphocytes, about 1.06; and platelets and plasma, about 1.03. If blood containing blood cells with different specific gravities is allowed to stand, a blood cell concentration gradient is formed according to the difference of the specific gravities. This property of blood is utilized in the blood filtration method of the present invention.

The first blood filtration method of the present invention comprises previously forming a blood cell concentration gradient in the storing unit to make the blood inhomogeneous, introducing the blood into a leukocyte-removing filter from the lower part of the storing unit, and then filtrating (this blood filtration method is hereinafter referred to as "first filtration method"). More specifically, the first filtration method of the present invention is suitable for filtering a whole blood product and comprises, in an inside of a storing unit represented by a blood bag for storing the whole blood product, causing first blood fraction containing a large amount of erythrocytes and leukocytes (granulocytes, monocytes) having a high specific gravity to precipitate in a lower part of a storing unit, causing a layer of second blood fraction containing a large amount of leukocytes (lymphocyte) having a low specific gravity so as to come above the first blood fraction, and causing third blood fraction containing a large amount of platelets and plasma to come above the second blood fraction, thereby previously making the whole blood product in the storing unit inhomogeneous with respect to the blood cell concentration, and introducing the blood to be processed into a leukocyte-removing filter from the lower part of the storing unit in the order of blood fractions in which the content of blood cells with a high specific gravity decreases. Further, the first filtration method of the present invention filters substantially all blood including in the storing unit using a single filter.

Normally, the blood is mixed to make the blood cell concentration homogeneous before filtering through the leukocyte-removing filter. The reason for homogenizing the blood is to prevent any part in the effective filtering area from being clogged up with micro aggregates contained in the blood at the initial stage of filtration. Since the micro aggregates are larger and heavier than blood cells, they precipitate in the lower part of the storing unit in an inhomogeneous state. If the blood in such an inhomogeneous state is filtered, precipitated micro aggregates come in contact with the filter at a comparatively early stage and, cause a part of the effective filtering area to become clogged up at an early stage of the filtration. This may unduly retard the filtration due to an uneven flow of blood and remarkably decrease the filter performance. Since the phenomenon has been thought to easily occur in blood preserved for several days or more, a method to start filtration after the blood has been homogenized as much as possible has been preferred. If a concentrated erythrocyte product with a small plasma content in an inhomogeneous state is filtered, erythrocytes with a high specific gravity precipitate to form a very viscous portion with a high hematocrit value (a volume percentage of erythrocytes in blood). When the blood is processed using a filter, this portion may not flow through the filter. If pressure is applied to forcibly filter the blood, the erythrocytes may be destructed by hemolysis. Because of these phenomena, filtration after making the blood as homogeneous as possible has been thought to be desirable to ensure a stable blood flow and constant leukocyte removing capability.

However, as a result of extensive studies using comparatively fresh whole blood products preserved at room temperature, the present inventors have found that the above problems are not observed even if a whole blood product is filtered in the order of blood cell concentration and a high content of erythrocytes and granulocytes is firstly filtered after a blood cell concentration gradient is formed to make the state of the blood inhomogeneous, and, surprisingly, the leukocyte removing capability is remarkably increased.

An additional surprising finding was a remarkable increase in a platelet recovery rate, when such an in homogenized whole blood product was filtered through a filter possessing a platelet recovering function.

As the reason why a liquid flow ability was unexpectedly obtained in the present invention even if a blood cell concentration gradient has been formed, a fresh whole blood product that has been preserved for only a very short period of time after collection has a small content of micro aggregates, and is thought not to cause the above-described problems due to micro aggregates. In addition, a large plasma content of a whole blood product as compared with a concentrated erythrocyte product makes it difficult to form unduly high viscous portions. This is supposed that a sufficient liquid flow ability has been acquired. However, the significant improvement in the leukocyte removal capability and the remarkable increase in the platelet recovery rate were unexpected effects. Although the mechanism for the change in the filtration performance due to in homogenization of a whole blood product is not known, the followings are thought to be possible reasons. When a whole blood product is in homogenized to cause erythrocytes and leukocytes with a higher specific gravity to be precipitated in the lower part of the storing unit, the blood fraction in this lower part contains a smaller amount of plasma. Since the filter material at the initial stage of filtration is not sufficiently covered with plasma proteins that suppress adhesion of blood cells such as albumin, when such blood is processed through a filter, the number of leukocytes caused to adhere to the surface of the filter material will increase, giving rise to improved leukocyte removing capability. On the other hand, platelets possessing a lower specific gravity are abundant in the upper layer of the inhomogenized whole blood product. When the platelets in the upper layer are caused to come in contact with the filter material, the surface of the filter would have already been covered with plasma proteins such as albumin, making it difficult for the platelets to be caused to adhere to the surface. This results in an increased platelet recovery rate.

The present inventors have further found that the platelet recovery rate can be greatly increased by the second filtration method comprising filling blood in a filter having a platelet recovering function, controlling the blood flow in such a manner that the flow rate is maintained at a low level or the blood flow is suspended for a predetermined period of time, and then filtering the blood (hereinafter referred to as "second filtration method").

More specifically, "the second filtration method" is suitable for processing a whole blood product or a platelet product such as a concentrated platelet product and platelet-rich plasma to remove leukocytes while allowing platelets to pass through and comprises filling a filter with homogeneous blood, controlling the blood flow by maintaining a low flow rate or suspending the flow for a predetermined period of time, causing a blood cell concentration gradient to be formed in the blood in a storing unit while said controlling the blood flow, releasing the flow rate control means to start filtration, and collecting the filtered blood from which leukocytes have been removed in a recovery unit such as a recovery bag. Both "the first filtration method" and "the second filtration method" employ one filter to process substantially all blood containing in a storing unit.

There are following two possible reasons for the remarkable increase in the platelet recovery rate by "the second filtration method". One is the same effect due to the blood cell concentration gradient formation as in the first filtration method. The flow control operation for a specific period of time after filling the filter with blood caused a blood cell concentration gradient to be formed in the blood in the storing unit. The other is the effect of plasma proteins such as albumin covering all over the surface of the filter material wetted with the blood during the flow control operation. The plasma proteins covering the surface of the filter material may make it difficult for platelets to be caused to adhere to the surface.

The term "fill the filter with blood" as used in the second filtration method in the present invention refers to an operation starting from the time when blood is introduced into the filter from the filter inlet port until the time when the blood comes out from the outlet port. Since it is desirable for increasing the platelet recovery rate to wet the entire filter with blood in said operation, the blood should be filled in the filter so that air does not remain in the filter as much as possible.

The term "controlling a flow rate" in the present invention indicates the operation of maintaining the blood flow rate at a low level or of suspending the flow of blood. Here, "maintaining the blood flow rate at a low level" indicates the conditions in which almost no blood flows, specifically, at a flow rate in terms of average linear velocity in the range of more than 0 cm/min to not more than 0.2 cm/min, and preferably more than 0 cm/min to not more than 0.1 cm/min, and "suspending the blood flow rate" indicates the conditions in which no blood flows, specifically, a flow rate in terms of average linear velocity of 0 cm/min. The term "average linear velocity" described above refers to a value obtained by dividing a blood flow rate (ml/min) by an effective filtering cross-sectional area (cm$^2$) of filter perpendicular to the direction of blood flow through which the blood can flow. A filter may include a plurality of filter materials with different effective filtering cross-sectional areas depending on the configuration of the filter. In such a case, an average of these effective filtering cross-sectional areas of the filter materials is used. In the present invention, either the control method of maintaining a low flow rate or the control method of suspending the blood flow can be employed after the filter has been filled with blood. Suspending the blood flow is more preferable due to simplicity of operation and the higher platelet recovery rate.

The flow rate control of the present invention can be carried out using a means functioning to retard or suspend the blood flow, for example, clamps such as a roller clamp, slide clamp, or Robert clamp, jigs that can deform a connecting tube by compression such as a forceps, and pumps that can control the linear velocity of blood. When using a jig that can compressively deform a connecting tube, the flow rate can be controlled at a low level by decreasing the diameter of the opening port by compressing the connecting tube or can be suspended by completely blocking the connecting tube.

"The first filtration method" and "the second filtration method" of the present invention are particularly suitable when the blood to be processed is a whole blood product. A whole blood product herein refers to a blood product processed by an artificial means such as an addition of an appropriate amount of an anticoagulant to collected whole blood. There are no specific limitations to the amount of the whole blood product to be filtered. More specifically, a whole blood product is a blood within three days, preferably within one day, and more preferably within eight hours after collection that contains an anticoagulant such as ACD (acid citrate dextrose) or CPD (citrate·phosphate·dextrose). In addition, the whole blood product is preferably preserved at a temperature of not less than 4° C. to less than 30° C., preferably not less than 15° C. to less than 25° C., until the product is filtered after collection. A whole blood product preserved for over three days and/or a whole blood product preserved at a temperature of 4° C. or less contains an increased amount of micro aggregates. Such a whole blood product may clog the filter with micro aggregates when inhomogenized, unpreferably resulting in an inadequate flow of blood. If preserved at a temperature above 30° C., unpreferably plasma proteins may easily be denatured.

The whole blood product having a blood cell concentration gradient used in "the first filtration method" and "the second filtration method" will be described in detail. It is preferable that the whole blood product having a blood cell concentration gradient have a hematocrit value in the lower part of the storing unit not less than 1.05 times to less than 2.50 times as much as the hematocrit value of the whole blood product in the storing unit that has been homogenized. If the hematocrit value in the lower part of the storing unit is less than 1.05 times as much as the hematocrit value of the blood that has been homogenized, formation of the blood cell concentration gradient is insufficient, whereby the leukocyte removing capability and platelet recovery rate tend not to be improved. If more than 2.50 times, an increase in the filtration time, hemolysis due to an increased pressure loss, and a remarkable decrease in the flow rate may occur because of the increased blood viscosity. A hematocrit value in the lower part of the storing unit is preferably not less than 1.05 times to less than 2.00 times, and particularly preferably not less than 1.20 times to less than 1.70 times, as much as the hematocrit value of the whole blood product that has been homogenized.

The hematocrit value of the whole blood product having a blood cell concentration gradient in the lower part of the storing unit is preferably not less than 35% to less than 75%. If the hematocrit value is less than 35%, formation of the blood cell concentration gradient is insufficient, whereby the leukocyte removing capability and platelet recovery rate may not be improved. If more than 75%, an increase in the filtration time, hemolysis due to an increased pressure loss, and a remarkable decrease in the flow rate may be induced. The more preferable range is not less than 45% to less than 65%.

The hematocrit value in the lower part of the storing unit is preferably measured on 2–3 ml of a sample directly collected from the lower part of the storing unit. When direct sample collection is difficult, first 2–3 ml of blood introduced into the tube connected to the storing unit when the whole blood product is filtered may be sampled and measured. The hematocrit value can be measured by a conventional method such as a centrifugal method (e.g. microhematcrit method), electric conductivity measurement, pulse wave height method, or measurement using an automatic blood cell counter.

The whole blood product having a blood cell concentration gradient used in "the first and second filtration methods" of the present invention preferably has a blood cell separation degree of not less than 3% to less than 60%, and more preferably not less than 10% to less than 45%. The blood cell separation degree used herein is a percentage of a liquid phase substance substantially not containing erythrocytes and containing plasma, platelets, and lymphocytes with a low specific gravity as main components in the total amount of the blood. If the blood cell separation degree is less than 3%, formation of the blood cell concentration gradient is insufficient, whereby the filter performance is not improved. If more than 60%, the hematocrit value in the lower part of the storing unit is excessively high, and an increase in the filtration time, hemolysis due to an increased pressure loss, and a remarkable decrease in the flow rate may be induced.

As the method for forming a blood cell concentration gradient in the whole blood product in "the first filtration method" in the present invention, a stationary method of allowing the blood preserved in the storing unit to stand and a centrifugal method of centrifuging the storing unit containing the whole blood product can be given.

To form a blood cell concentration gradient by the stationary method, the blood is preferably allowed to stand for not less than 5 minutes to less than 300 minutes. If less than 5 minutes, a sufficient blood cell concentration gradient may not be formed; if 300 minutes or more, the period of time allowed to stand may be excessively long, and the blood becomes difficult to be filtered. The more preferable period of time is not less than 10 minutes to less than 180 minutes, with a still more preferable time being not less than 30 minutes to less than 120 minutes.

To form a blood cell concentration gradient by centrifugation, weak centrifugation is preferable. For forming a blood cell concentration gradient by weak centrifugation, the blood is preferably centrifuged, except for the period of acceleration and deceleration, at a centrifugal force of about not less than 100×g to not more than 1,200×g, and especially preferably not less than 100×g to not more than 500×g, for 0.3 to 10 minutes. If the centrifugal force is less than this range, formation of the blood cell concentration gradient is insufficient. If more than this range, the high hematocrit value in the lower part of the storing unit may become high, and induce an increase in the filtration time due to increased viscosity. In addition, when the blood is filtered at a constant flow rate, a pressure loss may increase, giving rise to hemolysis of erythrocytes.

The whole blood product having a blood cell concentration gradient used in "the first filtration method" of the present invention can be prepared by either the above-described stationary method or the centrifugal method. The stationary method is more preferable due to the simple operation. When it is desirable to allow platelets to pass through, the centrifugal method tends to exhibit a somewhat small effect on the improvement in platelet recovery rate as compared with the stationary method, if the blood is filtered immediately after centrifugation. This is because platelets are somewhat activated by a stress of centrifugation. For this reason, a stationary period is preferably provided for a predetermined period of time after forming the blood cell concentration gradient by the centrifugal method to cause the activated platelets to become deactivated. The stationary period for deactivating the platelets is preferably not less than 5 minutes to less than 180 minutes, and more preferably not less than 10 minutes to less than 90 minutes.

In "the second filtration method" of the present invention, after filling the filter with the blood, the flow rate is controlled for a predetermined period of time, during which a blood cell concentration gradient is formed in the storing unit. The flow rate control period is preferably not less than 5 minutes to less than 300 minutes. If the flow rate control period is less than 5 minutes, the blood cell concentration gradient in the storing unit may be insufficiently formed. In addition, improvement of the platelet recovery rate may not be observed due to difficulty of a sufficient coverage of the filter material with plasma proteins. A flow rate control period of 300 minutes or more is unpreferably too long for the time controlling the flow rate to filter a large quantity of blood. The more preferable period of time is not less than 10 minutes to less than 180 minutes, with a most preferable time being not less than 30 minutes to less than 120 minutes.

"The second filtration method" of the present invention is effective not only when the blood to be filtered is a whole blood product, but also when a platelet product such as a concentrated platelet product and platelet-rich plasma product is filtered.

The platelet product such as a concentrated platelet product or platelet-rich plasma product used herein refers to a platelet product prepared by centrifuging collected whole blood product or a platelet product originating from a blood component collection. A platelet product within five days after preparation is preferable. In addition, such a platelet product is preferably preserved while shaking at room temperature of not less than 20° C. to less than 25° C. until the product is filtered after preparation. A platelet product preserved for more than five days or at a temperature outside of the above temperature range is not preferable due to the possibility of impaired platelet function.

A platelet product having a blood cell concentration gradient refers to a product having a leukocyte concentration in the lower part of the storing unit 1.05 times or more of the leukocyte concentration of the blood which has been homogenized. If less than 1.05 times, leukocyte removing capability tends to decrease. A more preferable range is not less than 1.20 times to less than 2.50 times.

The leukocyte concentration in the lower part of the storing unit can be measured by dying leukocyte nuclei and observing the dyed leukocyte nuclei using a microscope. In this instance, 2–3 ml of a blood sample is collected directly from the lower part of the storing unit or from 2–3 ml of a blood sample initially introduced into the tube connected to the storing unit.

The blood filtration method of the present invention is preferably carried out using the storing unit for storing blood, the recovery unit for collecting filtered blood, and hollow tubes connecting the storing unit/recovery unit with the filter. A sterile connecting device (SCD) may be used for connecting with tubes. There are no specific limitations to the tube used here inasmuch as the tube does not damage blood cells. Organic materials such as vinyl chloride, silicone, polysulfone, polyamide, polyester, urethane, polyethylene, and polypropylene are preferable due to excellent formability.

Any container that can store blood and is made of a material not activating blood cells or not inducing adhesion or denaturation of plasma proteins can be used as the storing unit for storing blood without specific limitations. Blood bags made of soft polyvinyl chloride or polyolefin commonly used for collecting and storing blood and syringes made of polypropylene, polyethylene, or polystyrene can be given as more specific examples.

Any container that can collect and store blood and is made of a material not activating blood cells and not inducing adhesion or denaturation of plasma proteins can be used as the recovery unit without specific limitations. The recovery unit may include at least one container for collecting each component separated by centrifugation of filtered blood. Blood bags made of soft polyvinyl chloride or polyolefin commonly used for collecting and storing blood can be given as more specific examples.

As the leukocyte-removing filter of the present invention, any known leukocyte-removing filter having inlet and outlet ports for blood and packed with a filter material that can capture and remove leukocytes in blood can be preferably used. More specifically, such a filter is a filter possessing a leukocyte removing capability of 2.30 or more, preferably 3.00 or more, wherein the leukocyte removing capability is defined as a logarithmic value of a value obtained by dividing the concentration of leukocytes remaining after filtration by the leukocyte concentration before filtration, i.e. −Log (leukocyte concentration after filtration/leukocyte concentration before filtration).

A fibrous medium, a sponge-like medium, and the like can be given as the filter material. With an objective of making the filter material easily wetted with blood, the surface of the filter material may be modified by coating a hydrophilic polymer or by radiation graft polymerization to the extent that blood is not adversely affected.

A material with low adherence to platelets may be introduced to the surface of the filter material to provide the leukocyte-removing filter with a platelet permeating function. As the material with low adherence to platelets, a polymer having a hydrophilic group and a chargeable group such as an amino group or carboxyl group and polyurethane as described in Japanese Patent Publication No. 06-51060 and Japanese Patent Application Laid-open No. 01-249063 can be given as suitable materials.

The blood filtration method of the present invention is a method for filtering blood using a leukocyte-removing filter. The blood may be filtered after providing an appropriate head drop using a blood bag or the like as a storing unit or may be filtered at a constant flow rate using a pump or the like.

A second object of the present invention is to provide an apparatus for automatically performing the blood filtration method such as "the first filtration method" or "the second filtration method" that requires an operation of allowing the blood to stand or of controlling the flow rate for a predetermined period of time before initiating blood filtration using a filter actually and to provide a blood filtration apparatus for performing "the first filtration method" and "the second filtration method" in stable filter performance while relieving burden loaded on an operator. The blood filtration apparatus of the present invention will be described in detail referring to the appended drawings. However, the blood filtration apparatus of the present invention is not limited to the specific embodiments described in the drawings.

Figure 1:
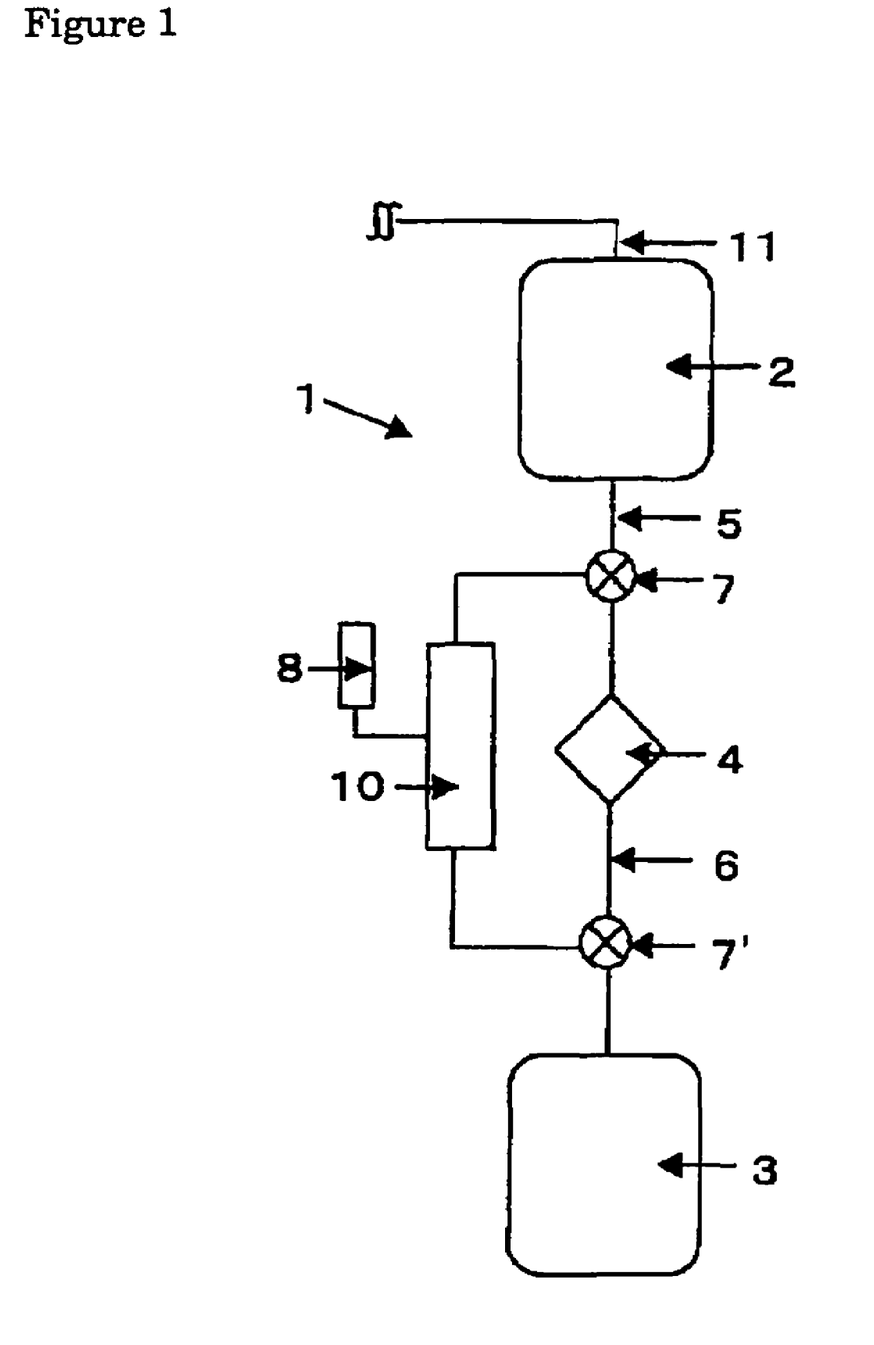
FIG. 1 is a schematic drawing showing an embodiment of the blood filtration apparatus of the present invention.
Figure 2:
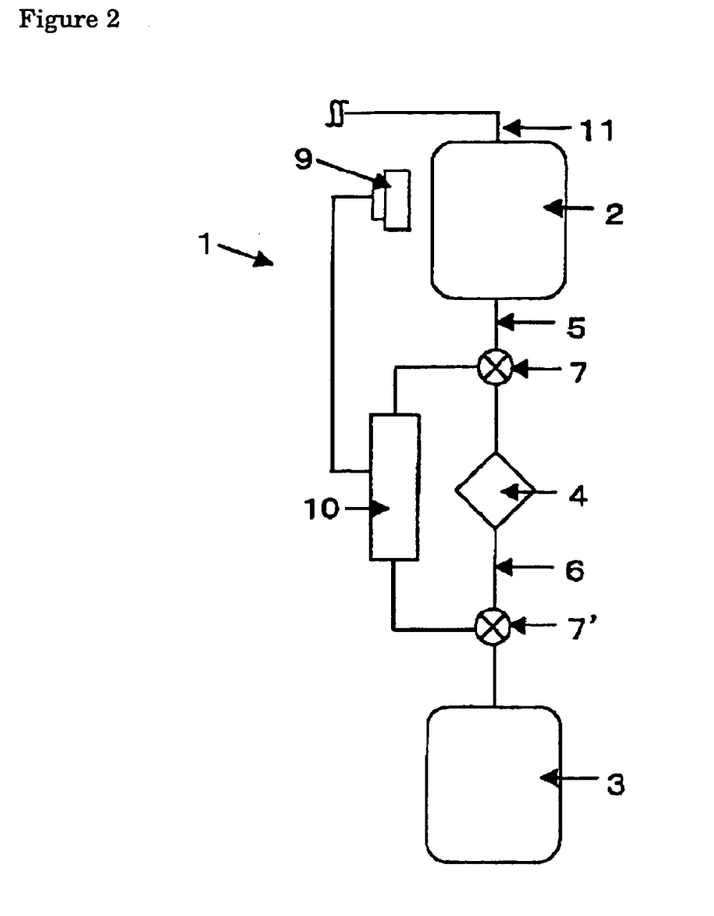
FIG. 2 is a schematic drawing showing another embodiment of the blood filtration apparatus of the present invention.
Figure 3:
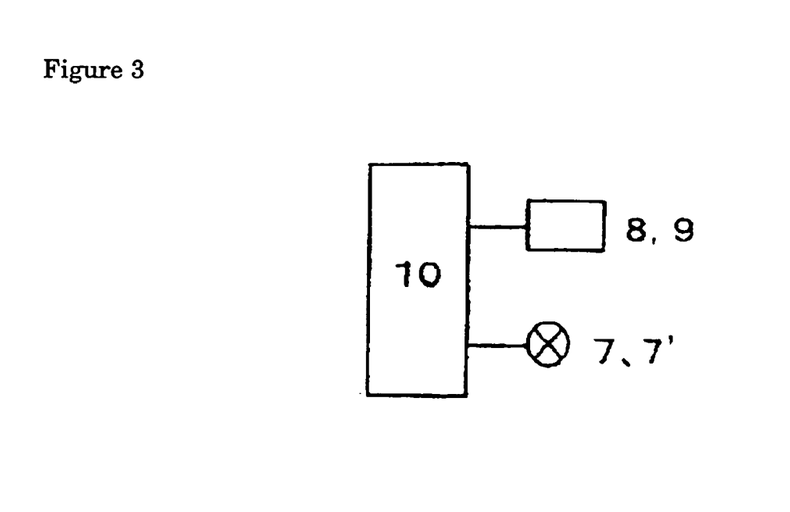
FIG. 3 is a block diagram of a control system of the blood filtration apparatus shown in FIGS. 1 and 2.

As shown in FIGS. 1 and 2, the blood filtration apparatus (1) of the present invention comprises a storing unit (2) for blood typified by a blood bag, a holding unit (11) for holding the storing unit (2) typified by a hook, a recovery unit (3), and a filter (4) having an inlet port and an outlet port for blood connected by hollow connecting tubes (5,6), and a flow rate controlling means (7,7') in the connecting tubes, of which the operation is automatically released by an operation means (10) based on signals emitted by signal transmitting means (8,9).

In the blood filtration apparatus (1) of the present invention, before the blood is actually processed through the filter (4), the blood flow is controlled at a low level or suspended by the flow rate controlling means (7,7') in the first connecting tube (5) and/or the second connecting tube (6) for a predetermined period of time so that the blood cannot substantially pass through. The blood flow control is automatically released when the operating means (10) recognizes the later-described signals emitted from the signal transmitting means (8,9) and sends the signals to the flow control means (7,7'), whereupon the filtration starts. Specifically, the flow control means (7,7'), the signal transmitting means (8,9), and the operating means (10) must work in conjunction with in the blood filtration apparatus (1) of the present invention. The term "work in conjunction with" herein refers to a state in which the signals from the signal transmitting means (8,9) can be automatically sent to the flow control means (7,7') via the operating means (10). This means that the flow control means (7,7'), the signal transmitting means (8,9), and the operating means (10) are electrically connected. The operating means (10) may be either a unit integrally formed with the signal transmitting means (8,9) and/or the flow control means (7,7') or an independent unit.

The signal transmitting means is an instrument capable of emitting signals to the operating means (10) when a predetermined period of time has elapsed or when a predetermined blood cell concentration gradient has been formed in the blood. As an example of the signal transmitting means (8) in FIG. 1, a timer that can release operation of the flow control means (7,7') after a predetermined period of time can be given. As a preferable example of the signal transmitting means (9) in FIG. 2, an optical sensor that can detect the state of formation of the blood cell concentration gradient (i.e., the blood cell separation degree) in the storing unit (2) and can work in conjunction with the flow control means (7,7') can be given.

The timer can be used either in "the first filtration method" or in "the second filtration method". In FIG. 1, when a timer is used as the signal transmitting means (8), the timer is set so that signals are emitted from the timer upon elapse of a predetermined period of time after causing the storing unit (2) to hold by the holding unit (11) and stand still or after the filter (4) has been filled with blood and the blood flow rate has been controlled. The signals are sent to the flow control means (7,7') via the operating means (10), whereupon the flow control means (7,7') are automatically released and filtration is initiated.

The optical sensor is a signal transmitting means that is particularly suitable for use when a whole blood product is filtered. In a blood filtration apparatus as shown in FIG. 2, when an optical sensor is used as the signal transmitting means (9) to filter a whole blood product, the optical sensor is set so that signals are emitted from the optical sensor when the sensor detects that a predetermined blood cell separation degree has been reached after the storing unit (2) has been caused to hold by the holding unit (11) and stand still and the blood cell concentration gradient has been formed. The signals are sent to the flow control means (7,7') via the operating means (10), whereupon the flow control means (7,7') are released.

Figure 4:
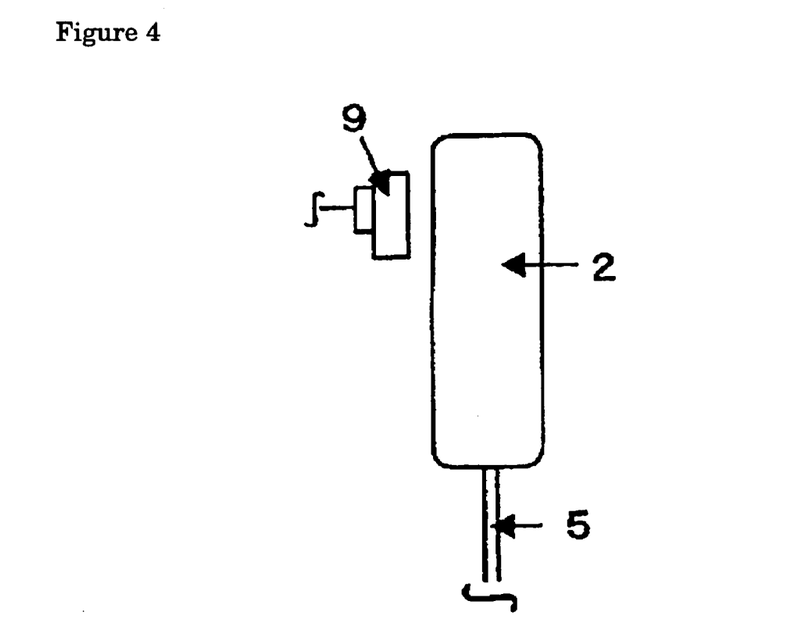
FIG. 4 is a partial side view of an embodiment of a sensor and a storing unit, wherein an optical sensor is used as a signal transmitting means.

As the optical sensor, a sensor optically detecting the location of a blood interface (for example, the interface of a layer containing a large amount of plasma, platelets, and lymphocytes with a low specific gravity and a layer containing a large amount of erythrocytes, granulocytes and monocytes with a high specific gravity) when the blood cell concentration gradient has been formed, as shown in FIG. 4, can be given. The sensor contains a photo emitting element and a photo acceptance element. Light emitted from the photo emitting element is reflected by blood and the reflected light is received by the sensor. When blood separation proceeds and the blood interface reaches the location at which the sensor is installed, the intensity of reflected light changes. Utilizing this principle, the sensor is installed at the location corresponding to an appropriate degree of blood cell separation so that signals are emitted from the sensor at the time when the intensity of reflected light has changed, whereby the flow control means (7,7') are automatically released to start blood filtration.

Figure 5:
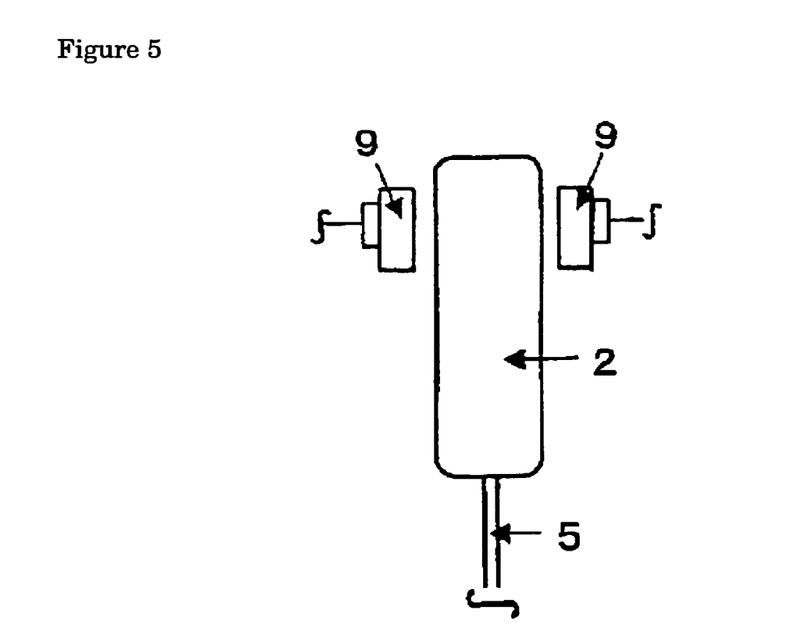
FIG. 5 is a partial side view of another embodiment of a sensor and a storing unit, wherein an optical sensor is used as a signal transmitting means.

As another example of the optical sensor, a device comprising a sensor having a photo emitting element and a sensor having a photo acceptance element, installed on both sides of the storing unit (2), as shown in FIG. 5, can be given. This type of sensor detects the intensity of transmitted light. When the blood interface reaches the location of the sensor, specifically when the intensity of transmitted light has increased, signals are emitted from the sensor, whereby the flow control means (7,7') are automatically released.

Figure 6:
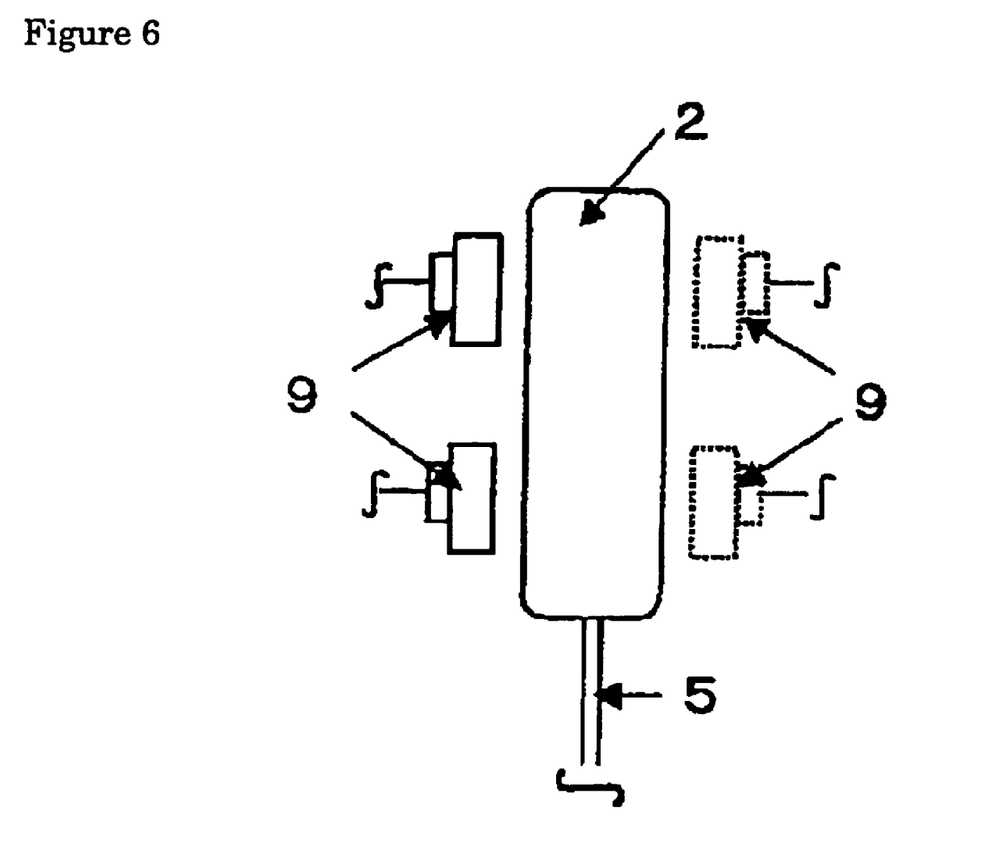
FIG. 6 is a partial side view of still another embodiment of a sensor and a storing unit, wherein an optical sensor is used as a signal transmitting means.

Alternatively, as shown in FIG. 6, sensors installed on the upper part and lower part of the storing unit can also be used in the present invention. The sensors are designed to emit signals when the difference in the intensity of reflected lights or transmitted lights from the upper part and lower part reaches a predetermined value, whereupon the flow control means (7,7') are automatically released.

Any device provided with a function of maintaining the blood flow rate at a low level or of suspending the blood flow, cooperating with the signal transmitting means (8,9) such as the above-described timer or optical sensor, and capable of automatically releasing the blood flow control based on the signals from the signal transmitting means (8,9) can be used without specific limitations as the flow rate controlling means (7,7') in the blood filtration apparatus of the present invention. Examples include a clamp, valve, and pump. The term "releasing the flow rate controlling means (7,7')" herein indicates, when the flow rate is controlled by compressing the connecting tube using a clamp or a valve, for example, expanding the opening diameter of the connecting tube to allow the blood to flow through. When the flow rate is controlled by a pump, the term "releasing the flow rate controlling means (7,7')" indicates initiating blood flow by operating the pump or increasing the blood flow rate by increasing the pump capacity.

Although the embodiments shown in FIGS. 1 and 2 are of the type in which the flow rate controlling means (7,7') are installed both in the first connecting tube (5) connecting the storing unit (2) with the filter (4) and in the second connecting tube (6) connecting the filter (4) with the blood recovery unit (3), the flow rate controlling means can be provided to either one of the connecting tubes.

A blood bag made of a soft material, if used as the storing unit (2), may be deformed and result in unstable detection of the interface by the optical sensor. A holder to stabilize the blood bag in a stable configuration can be provided to overcome this problem and to improve the precision of the sensor.

Any type of holder may be used as the holding unit (11) to hold the storing unit (2) of the present invention without a specific limitation to the extent that the holder can function to hold the storing unit in a predetermined position. A holder that can hold the storing unit standing still without causing vibration is particularly preferable. A hook or the like on which the storing unit is hung to provide a desired head drop can be given as a more specific example.

There are no specific limitations to the manner of filtration using the blood filtration apparatus (1) of the present invention. After automatically releasing operation of the flow rate controlling means (7,7') by the signal transmitting means (8,9) such as a timer or an optical sensor, blood may be filtered either by an appropriate head drop in the range of about 0.5–2 m or by a pump cooperating with the signal transmitting means (8,9).

When a whole blood product is filtered using the blood filtration method and/or blood filtration apparatus of the present invention, it is possible to prepare leukocyte-free blood component products from the whole blood product, from which leukocytes have been removed, by a known centrifugal method.

BEST MODE FOR CARRYING OUT THE INVENTION

The blood filtration method and blood filtration apparatus of the present invention will now be described in detail by way of examples, which should not be construed as limiting the present invention.

Examples of the first blood filtration method are given at the beginning.

EXAMPLE 1

(Leukocyte-Removing Filter)

The experiment was carried out using a nonwoven polyethylene terephthalate fabric with an average fiber diameter of 1.2 μm, the weight of the substrate per unit area (Metsuke) of 40 g/m$^2$, and a thickness of 0.2 mm, and a random copolymer of 2-hydroxyethyl methacrylate (HEMA) and dimethylaminoethyl methacrylate (DM) (mol ratio of HEMA:DM=97:3, hereinafter referred to as HM-3) as the material with low adherence to platelets.

(Synthesis of Polymer and Coating)

HM-3 polymer was prepared by random copolymerization of the monomers in ethanol (monomer concentration: 1 mol/l) in the presence of 1/200 mol/l of 2,2'-azobis(2,4-dimethylvaleronitrile) (V-65, manufactured by Wako Pure Chemical Industries, Ltd.) as an initiator for eight hours at 60° C.

The HM-3 polymer thus synthesized was coated on the surface of the nonwoven fabric according to the following procedure. The synthesized HM-polymer was dissolved in a mixed solvent of ethanol and water (weight ratio, ethanol:water=70:30) to prepare a liquid with a concentration of 7 g/dl. A specimen with a diameter of 25 mm punched from the nonwoven fabric was dipped in the polymer solution for one minute at 25° C. and filled in a holder made of polycarbonate. Dry nitrogen was passed though the holder for 4.5 minutes and the holder was dried under vacuum for 18 hours at 60° C., thereby coating the nonwoven fabric with the polymer.

(Preparation of Filter)

A filter for filtering blood was prepared by punching the nonwoven fabric to obtain packing disks with a diameter of 20 mm and packing 16 sheets of the packing disks in a container with an effective filtration cross-sectional area of 1.33 cm$^2$ having a blood inlet port and outlet port. When using the nonwoven fabric coated with HM-3, dry HM-3 coated nonwoven fabric was taken off from the polycarbonate holder and punched to obtain packing disks with a diameter of 20 mm. 16 packing disks thus obtained were stacked and packed.

(Blood Filtration Test: First Filtration Method)

A CPD-added whole blood product collected in a soft polyvinyl chloride blood bag and preserved at room temperature (20–25° C.) for 2–3 hours was sufficiently homogenized. 8 ml of the blood sample was collected using a syringe (brand name: Terumo Syringe® SS-20ESZ, manufactured by Terumo Corp.) from the homogenized whole blood product. The syringe containing the whole blood product was connected with a polyvinyl chloride tube with an internal diameter of 2.5 mm equipped with a clamp. The other end of the tube was connected with the blood inlet port of the above-described filter. The same tube was connected with the blood outlet port of the filter, with the other end of the tube being provided with a spit tube made of polyethylene for collecting blood discharged therefrom. Thereafter, a clamp provided between the syringe containing the whole blood product and the filter inlet port closed the, tube. After allowing the vertically placed syringe to stand for 60 minutes, the clamp was released and blood was filtered at a constant flow rate of 0.9 ml/min.

(Determination of Leukocyte Removing Capability and Platelet Recovery Rate)

The leukocyte concentration in a whole blood product before filtration was measured by an optical microscope after dying leukocytes in the blood sample collected from a homogeneous whole blood product with a Türk fluid. The leukocyte concentration in the whole blood product after filtration was measured by a fluorescence microscope after sampling a blood collected in the polyethylene spit tube and dying leaking leukocytes with an acridine orange solution. The leukocyte removing capability was determined from the leukocyte concentrations before and after the filtration according to the following formula.

Leukocyte removing capability=−Log(leukocyte concentration after filtration/leukocyte concentration before filtration)

For calculating the platelet recovery rate, the platelet concentrations before and after the filtration were determined using the same blood sample as the blood measured leukocyte concentration by a multi-purpose automatic blood cell counter (K-4500, manufactured by Sysmex Corp.). The platelet recovery rate was calculated according to the following formula.

Platelet recovery rate=(platelet concentration after filtration/platelet concentration before filtration)×100 (%)

(Determination of Hematocrit Value)

The hematocrit value of homogeneous blood (hereinafter referred to as Pre-Ht) and the hematocrit value at a lower part of the syringe (hereinafter referred to as Post-Ht) were determined as follows. To determine Pre-Ht, the whole blood product before processing with the filter remaining in the blood bag was sufficiently homogenized and 2 ml of sample blood was collected therefrom. Another similar syringe containing a whole blood product was prepared and allowed to stand for a predetermined period of time and 2 ml of blood was sampled from the lower part of the syringe for use to determine the Post-Ht of a whole blood product having a blood cell concentration gradient. In the Comparative Example described later, the whole blood product allowed to stand for a predetermined period of time was again homogenized and 2 ml of blood was sampled from the lower part of the syringe for use in the Post-Ht determination. A blood sample was put into a polyethylene spit tube and Pre-Ht and Post-Ht was determined using the same multi-purpose automatic blood cell counter as used for the determination of the platelet concentration.

As a result, Pre-Ht was 34%, Post-Ht was 52% (Post-Ht/Pre-Ht=1.53), the leukocyte removing capability was 3.72, and the platelet recovery rate was 84%.

EXAMPLE 2

The same whole blood, product was filtered using the same filter as used in Example 1 in the same manner as in Example 1, except that the standing-still period of time was five minutes. As a result, Post-Ht was 37% (Post-Ht/Pre-Ht=1.08), the leukocyte removing capability was 3.80, and the platelet recovery rate was 75%.

EXAMPLE 3

The same whole blood product was filtered using the same filter as used in Example 1 in the same manner as in Example 1, except that the standing-still period of time was 10 minutes. As a result, Post-Ht was 41% (Post-Ht/Pre-Ht=1.21), the leukocyte removing capability was 3.89, and the platelet recovery rate was 81%.

EXAMPLE 4

The same whole blood product was filtered using the same filter as used in Example 1 in the same manner as in Example 1, except that the standing-still period of time was 180 minutes. As a result, Post-Ht was 57% (Post-Ht/Pre-Ht=1.68), the leukocyte removing capability was 3.70, and the platelet recovery rate was 93%.

COMPARATIVE EXAMPLE 1

The same whole blood product as used in Example 1 was collected in a syringe and allowed to stand for 60 minutes. The blood was again homogenized to obtain a homogeneous whole blood product substantially having no blood cell concentration gradient. The whole blood product was filtered using the same filter as used in Example 1 in the same manner as in Example 1. As a result, Post-Ht was 35%, and equal to the Pre-Ht (Post-Ht/Pre-Ht=1.00). The leukocyte removing capability was 3.14 and the platelet recovery rate was 65%.

EXAMPLE 5

The experiment was carried out using a nonwoven polypropylene terephthalate fabric with an average fiber diameter of 1.4 μm, a Metsuke of 42 g/m$^2$, and a thickness of 0.22 mm and a random copolymer of HEMA and diethylaminoethyl methacrylate (DE) (mol ratio of HEMA:DE=95:5, hereinafter abbreviated to HE-5) as the material with low adherence to platelets. The HE-5 polymer was synthesized, the nonwoven fabric was coated, and blood was filtered in the same manner under the same conditions as in Example 1. As a result, the leukocyte removing capability was 3.65 and the platelet recovery rate was 85%.

EXAMPLE 6

The experiment was carried out using a random copolymer of hydroxypropyl methacrylate (HPMA) and DM (mol ratio of HPMA:DM=97:3, hereinafter referred to as PM-3) as the material with low adherence to platelets. The same nonwoven fabric was used as in Example 1, and PM-3 polymer were synthesized, the nonwoven fabric was coated, and blood was filtered in the same manner under the same conditions as in Example 1. As a result, the leukocyte removing capability was 3.74 and the platelet recovery rate was 88%.

EXAMPLE 7

The experiment was carried out using a random copolymer of HPMA, DM, and methoxydiethylene glycol methacrylate (DEG) (mol ratio of HPMA:DM:DEG=90:3:7, hereinafter referred to as PMD) as the material with low adherence to platelets. The same nonwoven fabric was used as in Example 1, and PMD polymer was synthesized, the nonwoven fabric was coated, and blood was filtered in the same manner under the same conditions as in Example 1. As a result, the leukocyte removing capability was 3.79 and the platelet recovery rate was 90%.

Comparing the results obtained in Examples 1–7 and Comparative Example 1, it can be seen that when a leukocyte-removing filter coated with a material with low adherence to platelets was used, not only the leukocyte removing capability, but also the platelet recovery rate was remarkably improved by forming a blood cell concentration gradient in the whole blood product.

EXAMPLE 8

A filter packed with the same nonwoven fabric as used in Example 1 not coated with a material with low adherence to platelets was prepared. A CPD-added whole blood product, three hours after collection, was collected in a syringe and allowed to stand for 60 minutes. The blood was filtered in the same manner as in Example 1. As a result, Pre-Ht was 39%, Post-Ht was 62% (Post-Ht/Pre-Ht=1.59), and the leukocyte removing capability was 4.34.

COMPARATIVE EXAMPLE 2

The same whole blood product as used in Example 8 was collected in a syringe and allowed to stand for 60 minutes. The blood was again homogenized to obtain a homogeneous whole blood product substantially having no blood cell concentration gradient. The whole blood product was filtered using the same filter as used in Example 8 in the same manner as in Example 8. As a result, Post-Ht was 39%, and equal to the Pre-Ht (Post-Ht/Pre-Ht=1.00). The leukocyte removing capability was 3.51.

Comparing the results obtained in Example 8 and Comparative Example 2, it can be seen that when a leukocyte-removing filter not coated with a material with low adherence to platelets was used, the leukocyte removing capability was remarkably improved by forming a blood cell concentration gradient.

EXAMPLE 9

A nonwoven fabric with an average fiber diameter of 12 μm, a Metsuke of 30 g/m$^2$, and a thickness of 0.2 mm (hereinafter referred to as prefilter), a nonwoven fabric with an average fiber diameter of 1.7 μm, a Metsuke of 66 g/m$^2$, and a thickness of 0.4 mm (hereinafter referred to as main filter A), and the same nonwoven fabric as used in Example 1 (hereinafter referred to as main filter B) were coated with HM-3 polymer. The following coating method was used. The nonwoven fabrics were cut into squares (length of one side: 10 cm) and were dipped in a solution dissolving HM-3 polymer at 25° C. for one minute. After removing excessive HM-3 solution on the nonwoven fabrics by compressing the nonwoven fabrics wetted with the HM-3 solution to a thickness of one half the wet thickness, the nonwoven fabrics were dried at room temperature for 24 hours, thereby coating the nonwoven fabrics with HM-3 polymer. The procedure was carried out for each sheet of coated nonwoven fabric until all sheets required for packing in the filter were obtained. A 5 g/dl HM-3 solution was used for coating the prefilter, whereas a 7 g/dl HM-3 solution was used for coating the main filters A and B.

The coated nonwoven fabrics thus obtained (two sheets of prefilter, two sheets of main filter A, and 28 sheets of main filter B) were packed in a polycarbonate container with an effective filtration cross-sectional area of 45 cm$^2$ in the order of the prefilter, main filter A, and main filter B from the inlet port side to the outlet port side. An objective filter was then prepared by ultrasonic welding.

A CPD-added whole blood product (450 ml) collected in a soft polyvinyl chloride blood bag and preserved at room temperature (22–24° C.) for 3 hours. The blood bag was connected to the inlet port of the above filter via a tube with an internal diameter of 2.9 mm to which a clamp was attached. The outlet port of the filter was connected with the blood recovery bag using the same tube. The blood bag containing the whole blood product was hung on a hook to provide a head drop of 1.0 m. After allowing to stand for 60 minutes, the clamp was released to collect filtered blood in the blood recovery bag. The hematocrit value was determined using a homogeneous blood sample and a sample collected from a lower part of the blood bag after the blood had been allowed to stand still for 60 minutes in the same manner as above. As a result of filtration, Pre-Ht was found to be 38%, Post-Ht was 54% (Post-Ht/Pre-Ht=1.42), the leukocyte removing capability was 4.12, and the platelet recovery rate was 87%.

EXAMPLE 10

The filtration was carried out according to the procedure of Example 9 with respect to the nonwoven fabrics, coating, filter, and method and conditions for filtration, except for using the same polymer with low adherence to platelets as used in Example 7. As a result, the leukocyte removing capability was 4.30 and the platelet recovery rate was 92%.

EXAMPLE 11

A fresh CPD-added whole blood collected in a soft polyvinyl chloride blood bag and preserved at room temperature for three hours was put into a centrifugal separator (CR7B3; manufactured by Hitachi Koki Co., Ltd.) and lightly centrifuged at 300×g of centrifugal force for five minutes to prepare a whole blood product (28 ml) having a blood cell concentration gradient. A filter was prepared by stacking and packing 16 sheets of nonwoven fabrics coated with HM-3 polymer, the same as those used in Example 1, in a holder with an internal diameter of 25 mm. The bag containing the whole blood product, in which a blood cell concentration gradient was formed by centrifugation, was connected with a polyvinyl chloride tube with an internal diameter of 2.5 mm. The other end of the tube was connected with the blood inlet port of the filter. The outlet port of the filter was connected with the blood bag for collecting the filtered whole blood product through the same tube. Pre-Ht was measured using a blood sample collected from homogeneous whole blood product before centrifugation and Post-Ht was measured using a blood sample collected from a lower part of the blood bag containing a whole blood product that had been allowed to stand for five minutes after centrifugation. As a result, Pre-Ht was 32% and Post-Ht was 63% (Post-Ht/Pre-Ht=1.97).

After connecting with the filter, the blood bag containing the whole blood product having a blood cell concentration gradient was suspended to provide a head drop of 40 cm for filtration. The blood was filtered. As a result, the leukocyte removing capability was 3.48 and the platelet recovery rate was 76%.

EXAMPLE 12

A fresh CPD-added whole blood product preserved for four hours at room temperature after collection was centrifuged in the same manner as in Example 11 and allowed to stand still for 60 minutes. Except for the above procedure, the filtration was carried out using the same nonwoven fabrics, coating, and filter as used in Example 11 in the same manner as in Example 11. As a result, Pre-Ht was 37%, Post-Ht was 66% (Post-Ht/Pre-Ht=1.78) the leukocyte removing capability was 3.69, and the platelet recovery rate was 82%.

Examples of the second filtration method will now be described.

EXAMPLE 13

The experiment for the second filtration method was carried out using the same nonwoven fabric, polymer with low adherence to platelets, and filter as used in Example 1. The leukocyte removing capability and platelet recovery rate were determined in the same manner as in Example 1.

(Blood Filtration Test: Second Filtration Method)

A CPD-added whole blood product collected in a soft polyvinyl chloride blood bag and preserved at room temperature (20–25° C.) for 2–3 hours was sufficiently homogenized. 8 ml of a blood sample was collected from this product using a syringe (brand name: Terumo Syringe® SS-20ESZ, manufactured by Terumo Corp.). The syringe containing the whole blood product was connected with a polyvinyl chloride tube with an internal diameter of 2.5 mm. The other end of the tube was connected with the blood inlet port of the above-described filter. The same tube but equipped with a clamp was connected with the blood outlet port of the filter. A soft polyvinyl chloride bag was arranged as a blood recovery bag to collect blood discharged from the other end of the filter. The whole blood product in a syringe was sufficiently homogenized and filled in the filter at a constant linear velocity of 0.68 cm/min (a flow rate of 0.9 ml/min). The pump was stopped when the blood came from the outlet port of the filter. The tube was closed using the clamp at a point between the filter and the recovery bag to suspend blood flow for 60 minutes. Then, the clamp was released to run the pump again and filter the blood at a constant linear velocity of 0.68 cm/min. As a result, the leukocyte removing capability was 3.58 and the platelet recovery rate was 92%.

EXAMPLE 14

A whole blood product was filtered using the same filter as used in Example 13 in the same manner as in Example 13, except that the blood flow was suspended for five minutes. As a result, the leukocyte removing capability was 3.60 and the platelet recovery rate was 83%.

EXAMPLE 15

A whole blood product was filtered using the same filter as used in Example 13 in the same manner as in Example 13, except that the blood flow was suspended for one minute. As a result, the leukocyte removing capability was 3.62 and the platelet recovery rate was 76%.

COMPARATIVE EXAMPLE 3

A whole blood product was filtered using the same filter as used in Example 13 in the same manner as in Example 13, except that the blood flow was not suspended after the blood was filled in the filter. As a result, the leukocyte removing capability was 3.64 and the platelet recovery rate was 64%.

COMPARATIVE EXAMPLE 4

The same filtration experiment as in Example 13 was carried out using the same filter as in Example 13, except that a physiological saline solution was filled in the filter instead of the blood. As a result, the leukocyte removing capability was 3.50 and the platelet recovery rate was 69%.

EXAMPLE 16

The filtration was carried out in the same manner under the same conditions as in Example 13 using the same nonwoven fabric, polymer, and filter as in Example 5. As a result, the leukocyte removing capability was 3.48 and the platelet recovery rate was 93%.

EXAMPLE 17

A filtration experiment was carried out under the following conditions using the same filter as used in Example 9.

A CPD-added whole blood product (450 ml) collected in a soft polyvinyl chloride blood bag and preserved at room temperature (22–24° C.) for four hours was sufficiently homogenized. The blood bag was connected with the blood inlet port of the filter using a tube equipped with a clamp. The blood outlet port of the filter was connected with the blood recovery bag using the same tube. The bag containing the whole blood product was located at a height to provide a head drop of 1.0 m. The clamp was closed at the time when the filter was filled with a homogeneous whole blood product to suspend the flow of blood for 60 minutes. Then, the clamp was released to filter the blood. As a result, the leukocyte removing capability was 3.64 and the platelet recovery rate was 95%.

EXAMPLE 18

The same filter as in Example 13 was filled with the same whole blood product as in Example 13 at a constant linear velocity of 0.68 cm/min. Thereafter, the setting of the pump was changed to maintain a linear velocity of 0.08 cm/min for five minutes. After setting back the linear velocity to 0.68 cm/min by changing the setting of the pump again, the blood was filtered. As a result, the leukocyte removing capability was 3.61 and the platelet recovery rate was 78%.

EXAMPLE 19

A filter with an effective filtration cross-sectional area of 1.33 $cm^2$ was prepared by packing 14 sheets of the nonwoven fabrics coated with HM-3 prepared in the same manner as in Example 13 in a container having an inlet port and an outlet port. 8 ml of a concentrated platelet product, prepared by centrifuging a CPD-added whole blood product and preserved for three days at 22–24° C. while shaking, was collected in a syringe and sufficiently homogenized. The platelet product was then filtered in the same manner as in Example 13, provided that the concentrated platelet product was filled in the filter using a pump at a constant linear velocity of 0.92 cm/min (flow rate: 1.2 ml/min) and, after suspending the flow of the concentrated platelet product for 30 minutes, the platelet product was filtered at a constant linear velocity of 0.92 cm/min. The leukocyte removing capability and platelet recovery rate were determined in the same manner as in Example 1. As a result, the leukocyte removing capability was 3.20 and the platelet recovery rate was 88%.

The manner of operation and preferable conditions of blood filtration using the blood filtration apparatus of the present invention will be described below.

EXAMPLE 20

When the first filtration method is carried out using the blood filtration apparatus shown in FIG. 1 in which a timer is used as a signal transmitting means (8), a flow rate controlling means (7,7') is firstly closed, and a blood storing unit (2) filled with blood is hung on a hook. After hooking the blood storing unit (2), a timer is set. After elapsing of the time previously set by the timer, the flow rate controlling means (7,7') are released by an operation means (10) based on signals from the timer to automatically start the blood to flow. The blood from which leukocytes have been removed by flowing through a leukocyte-removing filter (4) is collected in a blood recovery unit (3). The period until the time when the flow rate controlling means (7,7') are automatically released by the timer from the time when the blood storing unit (2) is hung on a hook is preferably not less than 5 minutes to less than 300 minutes, more preferably not less than 10 minutes to less than 180 minutes, and still more preferably not less than 30 minutes to less than 120 minutes. If less than five minutes, a sufficient blood cell concentration gradient may not be formed; if 300 minutes or more, it is difficult to filter a large amount of blood.

When blood in which a blood cell concentration gradient has been formed by the centrifugal method is filtered, to inactivate the platelets that have been activated by centrifugation, the timer is preferably set to automatically release the flow rate controlling means (7,7') at not less than 5 minutes to less than 180 minutes, and preferably not less than 10 minutes to less than 90 minutes, after the centrifuged blood is hung on a hook.

EXAMPLE 21

When the second filtration method is carried out using the blood filtration apparatus shown in FIG. 1 in which a timer is used as the signal transmitting means (8), the blood storing unit (2) filled with blood is hung on a hook. Next, the flow rate controlling means (7,7') are opened to fill the leukocyte-removing filter (4) with blood. When the leukocyte-removing filter (4) has been filled with blood, the flow rate controlling means (7,7') are closed and the timer is set. When elapsing of the time previously set by the timer, the flow rate controlling means (7,7') are released by the operation means (10) based on signals from the timer to automatically start the blood to flow. The blood from which leukocytes have been removed by flowing through the leukocyte-removing filter (4) is collected in the blood recovery unit (3).

The period of time for which the blood flow rate is controlled after the filter has been filled with blood is preferably not less than 5 minutes to less than 300 minutes, more preferably not less than 10 minutes to less than 180 minutes, and still more preferably not less than 30 minutes to less than 120 minutes. If the flow rate control time is less than five minutes, the effect of filling the filter with blood cannot be obtained and an increase in the platelet recovery rate may not be achieved. If 300 minutes or more, it is difficult to filtrate a large quantity of blood.

EXAMPLE 22

When the first filtration method is carried out using the blood filtration apparatus as shown in FIG. 2 in which an optical sensor is used as the signal transmitting means (9), a blood storing unit (2) is filled with blood and hung on a hook, with the flow control means (7,7') being maintained closed. When the optical sensor detects the blood separation degree set previously, the flow rate controlling means (7,7') are automatically released by an operation means (10) based on signals from the optical sensor to start the blood to flow. The blood from which leukocytes have been removed by flowing through a leukocyte-removing filter (4) is collected in the blood recovery unit (3). The blood cell separation degree is preferably not less than 3% to less than 60%, and more preferably not less than 10% to less than 45%. If the blood cell separation degree is less than 5%, formation of the blood cell concentration gradient is insufficient, whereby the filter performance is not improved. If more than 60%, the hematocrit value in the lower part of the storing unit may excessively high, and an increase in the filtration time, hemolysis due to an increased pressure loss, or a remarkable decrease in the flow rate may be potentially induced.

INDUSTRIAL APPLIABILITY

According to the blood filtration method of the present invention, leukocytes can be efficiently removed from a whole blood product. In addition, a high platelet recovery rate can be attained in a stable manner while efficiently removing leukocytes from a whole blood product or platelet product. Since the blood filtration method of the present invention can highly remove leukocytes that cause transfusion side effects and can recover platelets as an effective component at a high yield, the method can be used as an effective method in blood transfusion medical treatment.

The blood filtration apparatus of the present invention is particularly suitable for carrying out the blood filtration method of the present invention. Since the blood filtration apparatus of the present invention starts the filtration after the flow rate controlling means has been automatically released, it can relieve burden loaded on the operators and increase and stabilize the filter performance.

The invention claimed is:

1. A blood filtration method for removing leukocytes from blood comprising:
    forming a blood cell concentration gradient in a storing unit for storing the blood;
    filtering all blood components in the order of said blood cell concentration gradient in said storing unit through only one leukocyte-removing filter from a lower part of said storing unit; and collecting the filtered blood components in a recovery unit,
wherein said blood cell concentration gradient is formed by allowing the blood to stand for a predetermined period of time, and
wherein the blood is a fresh whole blood product.

2. The blood filtration method according to claim 1, wherein the blood cell concentration gradient is previously formed in the storing unit before filling the filter with blood.

3. The blood filtration method according to claim 1, wherein the blood cell concentration gradient is formed by allowing the blood to stand for not less than 5 minutes to less than 300 minutes.

4. The blood filtration method according to claim 1, wherein the blood cell concentration gradient is formed in the storing unit after filling the filter with blood.

5. The blood filtration method according to claim 1, wherein the blood cell concentration gradient is formed by controlling the blood flow rate for a predetermined period of time.

6. The blood filtration method according to claim 5, wherein the blood cell concentration gradient is formed by controlling the blood flow rate over not less than 5 minutes to less than 300 minutes.

7. The blood filtration method according to claim 1, wherein the blood is introduced into the leukocyte-removing filter from a lower part of the storing unit after forming an erythrocyte concentration gradient so that the hematocrit value of the blood in the lower part of the storing unit is larger than the hematocrit value of the whole blood product in the storing unit that has been uniformly homogenized.

8. The blood filtration method according to claim 7, wherein the hematocrit value of the blood in the lower part of the storing unit is not less than 1.05 times to less than 2.50 times the hematocrit value of the whole blood product in the storing unit that has been uniformly homogenized.

9. The blood filtration method according to claim 7, wherein the hematocrit value of the blood in the lower part of the storing unit is not less than 35% to less than 75%.

10. The blood filtration method according to claim 1, wherein a blood cell separation degree of the blood in the storing unit after forming the blood cell concentration gradient is not less than 3% to less than 60%.

11. The blood filtration method according to claim 1, wherein leukocytes are selectively removed and platelets are allowed to pass through.

* * * * *